(12) United States Patent  
McDougal et al.

(10) Patent No.: US 8,361,455 B2
(45) Date of Patent: Jan. 29, 2013

(54) NON-LITHOTRIPSIC KIDNEY-STONE THERAPY

(75) Inventors: W. Scott McDougal, Manchester, MA (US); Dianne E. Sacco, Charlestown, MA (US); Alexander Schwarz, Brookline, MA (US); Jean-Marie Vogel, Lincoln, MA (US)

(73) Assignees: Pluromed, Inc., Woburn, MA (US); The General Hospital Corporation, Boston, MA (US)

( * ) Notice: Subject to any disclaimer, the term of this patent is extended or adjusted under 35 U.S.C. 154(b) by 1857 days.

(21) Appl. No.: 11/412,407

(22) Filed: Apr. 27, 2006

(65) Prior Publication Data

US 2006/0269512 A1 Nov. 30, 2006

Related U.S. Application Data

(60) Provisional application No. 60/676,757, filed on May 2, 2005.

(51) Int. Cl.
*A61K 31/77* (2006.01)
(52) U.S. Cl. ............... 424/78.38; 424/78.08; 424/78.34; 424/78.37; 606/2.5
(58) Field of Classification Search ............... 424/78.38, 424/78.17, 78.08
See application file for complete search history.

(56) References Cited

U.S. PATENT DOCUMENTS

| 4,608,979 | A | 9/1986 | Breidenthal et al. |
| 5,403,324 | A | 4/1995 | Ciervo et al. |
| 5,860,872 | A | 1/1999 | Vitale |
| 5,860,972 | A | 1/1999 | Hoang |
| 6,565,530 | B2 | 5/2003 | Sahatjian et al. |
| 2002/0119116 | A1 | 8/2002 | Sahatjian et al. |
| 2002/0120237 | A1 | 8/2002 | Sahatjian et al. |
| 2004/0266983 | A1 | 12/2004 | Reeve et al. |
| 2005/0053662 | A1 | 3/2005 | Sahatjian et al. |
| 2005/0175702 | A1 | 8/2005 | Muller-Schulte |
| 2005/0203498 | A1 | 9/2005 | Mon et al. |

FOREIGN PATENT DOCUMENTS

| EP | 0 645 150 | 3/1995 |
| WO | WO-00/44323 | 8/2000 |
| WO | WO-2005/037062 | 4/2005 |

OTHER PUBLICATIONS

Database WPI, Section Ch, Week 200059, Derwent Publications Ltd., London, GB; AN 1995-175365, XP002397589 & JP 03 107488 B2 (Shiseido Co Ltd.) Nov. 6, 2000 Abstract Only.
International Search Report dated Sep. 25, 2006 from PCT/US2006/016208.

*Primary Examiner* — James Rogers
(74) *Attorney, Agent, or Firm* — Hamilton, Brook, Smith & Reynolds, P.C.

(57) ABSTRACT

One aspect of the present invention relates to a method of using peristalsis to force a polymer plug through a mammalian lumen, thereby removing any calculi and/or calculi fragments present in the lumen. In one embodiment, the method is used as an alternative to conventional lithotripsy. In another embodiment, the method is used in conjunction with lithotripsy, thereby removing the small calculi fragments that result from such procedures.

37 Claims, 5 Drawing Sheets

NON-LITHOTRIPSIC KIDNEY-STONE THERAPY

RELATED APPLICATIONS

This application claims the benefit of priority to U.S. Provisional Patent Application Ser. No. 60/676,757, filed May 2, 2005.

BACKGROUND OF THE INVENTION

Lithiasis is a common human ailment characterized by calculi or "stones" formed within a passage of the human body. While stones have been documented in just about every passage within the body, kidney stones (nephrolithiasis) and gallstones (cholelithiasis) remain the most common. Regardless of its location, however, a stone is typically an extremely hard and unyielding mass which blocks the passage (e.g., lumen) in which it presents.

Calculi or stones in the urinary tract or kidneys usually arise because of the breakdown of a delicate balance in the body. Specifically, the kidneys must conserve water to function, but they must excrete materials that have a low solubility. These opposing requirements must be balanced during adaptation to diet, climate and activity. The problem is mitigated to some degree because urine contains substances that inhibit crystallization of stone-forming minerals. However, when urine becomes supersaturated with insoluble materials, because excretion rates are excessive and/or because water conservation is extreme, crystals form and may grow and aggregate to form a stone.

Although small crystals are readily voided from the kidney with urine, the larger stones frequently become dislodged from the kidney and enter the ureter or occlude the uretero-pelvic junction, causing obstruction and pain. Although some stones can ultimately traverse the ureter, their passage typically produces pain and bleeding. Usually, the pain is so severe that narcotic drugs are needed for its control.

Removal of stones from the kidneys or urinary tract can be effected medically, mechanically or surgically. A well-known surgical approach involves passing a flexible basket in a retrograde manner up the ureter from the bladder, and using the basket to capture the stones. However, the baskets require post-capture removal and only work well for medium-sized stones. Surgery has also been used to remove kidney stones, especially so-called staghorn stones which get lodged in the ureter.

Another surgical technique, percutaneous ultrasonic lithotripsy, requires the passage of a rigid cystoscopy-like instrument in the renal pelvis through a small incision in the flank whereupon stones are broken up by a small ultrasound transducer and then removed directly. Another surgical technique is laser lithotripsy via a ureteroscope. All of these procedures, which can be quite painful, are elaborate and expensive, and they do not always result in complete removal of the stones and fragments. One non-invasive technique, known as extracorporeal lithotripsy, entails transmission of high-intensity shock waves from outside the body to fragment the stones within the body. The resulting stone fragments are then voided with urine.

Stents have also been used to decompress ureteral obstructions, ensuring that urine drains from the kidney to the bladder. It was recognized that placement of a stent within the ureter could help small stones and stone fragments to transit the ureter. In a typical procedure involving a stent, a guide wire is passed through the ureter to the renal pelvis. A hollow, flexible, cylindrical stent is then advanced with a pusher over the guide wire. The guide wire and pusher are then extracted from the stent and the body, leaving an open lumen for urine to pass through. However, because the lumen defined by the cylindrical stent is even smaller than the ureter itself, all but the smallest stones and sludge are precluded from passing through. In many cases, stone fragments often block the open stent passageway.

SUMMARY OF THE INVENTION

One aspect of the present invention provides an approach to the treatment of lithiasis. In one embodiment, the instant invention provides a method of using peristalsis to force a polymer plug through a mammalian lumen, thereby removing any calculi and/or calculi fragments present in the lumen. In one embodiment this method is used as an alternative to conventional lithotripsy. In another embodiment this method is used subsequent to lithotripsy, removing the small fragments that result from such procedures. In certain embodiments, the polymer plug is generated in situ by one or more physical phenomena, such as temperature, pH change and/or ionic interactions. In certain embodiments the polymer plug rapidly dissolves after passing through the lumen.

DETAILED DESCRIPTION OF THE INVENTION

One aspect of the present invention provides an approach to the treatment of lithiasis. Importantly, the present invention mitigates the risk of damage to surrounding body tissue when removing a calculi (e.g., biological concretions such as urinary, biliary, and pancreatic stones) which obstructs or may otherwise be present within a body's anatomical lumen. Remarkably, the present invention improves significantly the treatment of lithiasis, while simultaneously reducing the risk of tissue damage and decreasing the procedure time.

In one embodiment, the instant invention provides a method of using a non-tissue adhesive polymer plug to partially or completely occlude a lumen and using the plug to remove calculi and/or calculi fragments from the lumen through the passage of the polymer plug through the lumen due to the natural action of peristalsis on the polymer plug. In one embodiment the method is used as an alternative to conventional lithotripsy. In another embodiment the method is used subsequent to lithotripsy, to remove the small fragments that result from such procedures. In certain embodiments the polymer plug is generated in situ by one or more physical phenomena, such as temperature, pH changes and/or ionic interactions. In some of these embodiments a dual lumen catheter is utilized to inject two solutions proximal to the stone, the mixing of said solutions causing a polymer plug to form. In certain embodiments the polymers used in the methods of the invention are inverse thermosensitive polymers. In other embodiment, gel formation due to ionic charges may be used to form a polymer plug. In certain embodiments the polymer plug rapidly dissolves, e.g., in the bladder, after being passed through the lumen.

Definitions

For convenience, certain terms employed in the specification, exemplification, and appended claims are collected here.

The articles "a" and "an" are used herein to refer to one or to more than one (i.e., to at least one) of the grammatical object of the article. By way of example, "an element" means one element or more than one element.

The terms "reversibly gelling" and "inverse thermosensitive" refer to the property of a polymer wherein gelation takes place upon an increase in temperature, rather than a decrease in temperature.

The term "transition temperature" refers to the temperature or temperature range at which gelation of an inverse thermosensitive polymer occurs.

The term "contrast-enhancing" refers to materials capable of being monitored during injection into a mammalian subject by methods for monitoring and detecting such materials, for example by radiography or fluoroscopy. An example of a contrast-enhancing agent is a radiopaque material. Contrast-enhancing agents including radiopaque materials may be either water soluble or water insoluble. Examples of water soluble radiopaque materials include metrizamide, iopamidol, iothalamate sodium, iodomide sodium, and meglumine. Examples of water insoluble radiopaque materials include metals and metal oxides such as gold, titanium, silver, stainless steel, oxides thereof, aluminum oxide, zirconium oxide, etc.

As used herein, the term "polymer" means a molecule, formed by the chemical union of two or more oligomer units. The chemical units are normally linked together by covalent linkages. The two or more combining units in a polymer can be the same, in which case the polymer is referred to as a homopolymer. They can be also be different and, thus, the polymer will be a combination of the different units; these polymers are referred to as copolymers.

As used herein, "crosslinking" is when individual polymer chains are linked together by covalent bonds ("chemical crosslinking") or ionic bonds ("ionic crosslinking") to form a three dimensional network. In certain polymers this kind of process has the effect of producing a gel.

The term "biocompatible", as used herein, refers to having the property of being biologically compatible by not producing a toxic, injurious, or immunological response in living tissue. The term "non-tissue adhesive", as used herein denotes a substance (e.g. a polymer plug) does not adhere to biological tissue.

The term "poloxamer" denotes a symmetrical block copolymer, consisting of a core of PPG polyoxyethylated at both of its terminal hydroxyl groups, i.e., conforming to the interchangeable generic formula $(PEG)_X$-$(PPG)_Y$-$(PEG)_X$ and $(PEO)_X$-$(PPO)_Y$-$(PEO)_X$. Each poloxamer name ends with an arbitrary code number, which is related to the average numerical values of the respective monomer units denoted by X and Y.

The term "poloxamine" denotes a polyalkoxylated symmetrical block copolymer of ethylene diamine conforming to the general type $[(PEG)_X\text{-}(PPG)_Y]_2\text{-}NCH_2CH_2N\text{-}[(PPG)_Y\text{-}(PEG)_X]_2$. Each Poloxamine name is followed by an arbitrary code number, which is related to the average numerical values of the respective monomer units denoted by X and Y.

The term "inverse thermosensitive polymer" as used herein refers to a polymer that is soluble in water at ambient temperature, but at least partially phase-separates out of water at physiological temperature. Inverse thermosensitive polymers include poloxamer 407, poloxamer 188, Pluronic® F127, Pluronic® F68, poly(N-isopropylacrylamide), poly(methyl vinyl ether), poly(N-vinylcaprolactam); and certain poly(organophosphazenes). See *Bull. Korean Chem. Soc.* 2002, 23, 549-554.

"Alginic acid" as used here in is a naturally occurring hydrophilic colloidal polysaccharide obtained from the various species of brown seaweed (Phaeophyceae). It occurs in white to yellowish brown filamentous, grainy, granular or powdered forms. It is a linear copolymer consisting mainly of residues of β-1,4-linked D-mannuronic acid and α-1,4-linked L-glucuronic acid. These monomers are often arranged in homopolymeric blocks separated by regions approximating an alternating sequence of the two acid monomers, as shown below:

The formula weight of the structural unit is 176.13 (theoretical; 200 is the actual average). The formula weight of the macromolecule ranges from about 10,000 to about 600,000 (typical average).

"Sodium alginate" and "potassium alginate" are salts of alginic acid. For example, "potassium alginate" is shown below:

"Gellan gum" is a high molecular weight polysaccharide gum produced by a pure culture fermentation of a carbohydrate by Pseudomonas elodea, purified by recovery with isopropyl alcohol, dried, and milled. The high molecular weight polysaccharide is principally composed of a tetrasaccharide repeating unit of one rhamnose, one glucuronic acid, and two glucose units, and is substituted with acyl (glyceryl and acetyl) groups as the O-glycosidically-linked esters. The glucuronic acid is neutralized to a mixed potassium, sodium, calcium, and magnesium salt. It usually contains a small amount of nitrogen containing compounds resulting from the fermentation procedures. It has a formula weight of about 500,000. "Sodium gellan" and "potassium gellan" are salts of gellan gum.

Carboxymethylcellulose (CMC) is a polymer derived from natural cellulose. Unlike cellulose, CMC is highly water-soluble. The CMC structure is based on the b-(1®4)-D-glucopyranose polymer of cellulose. Different preparations may have different degrees of substitution, but it is generally in the range 0.6-0.95 derivatives per monomer unit, as shown below:

CMC molecules are somewhat shorter, on average, than native cellulose with uneven derivatization giving areas of high and low substitution. This substitution is mostly 2-O— and 6-O-linked, followed in order of importance by 2,6-di-O— then 3-O—, 3,6-di-O—, 2,3-di-O— lastly 2,3,6-tri-O-linked. It appears that the substitution process is a slightly cooperative (within residues) rather than random process giving slightly higher than expected unsubstituted and trisubstituted areas. CMC molecules are most extended (rod-like) at low concentrations but at higher concentrations the molecules overlap and coil up and then, at high concentrations, entangle to become a thermoreversible gel. Increasing ionic strength and reducing pH both decrease the viscosity as they cause the polymer to become more coiled. The average chain length and degree of substitution are of great importance; the more-hydrophobic lower substituted CMCs are thixotropic but more-extended higher substituted CMCs are pseudoplastic. At low pH, CMC may form cross-links through lactonization between carboxylic acid and free hydroxyl groups.

"Poly vinyl alcohol" (PVA) is a water soluble polymer synthesized by hydrolysis of a poly vinyl ester such as the acetate and used for preparation of fibers. PVA a thermoplastic that is produced from full or partial hydrolysis of vinyl ester such as vinyl acetate resulting in the replacement of some or all of the acetyl groups with hydroxyl groups. For example:

In certain embodiments polyvinyl alcohol (PVA) is a synthetic resin produced by polymerisation of vinyl acetate (VAM) followed by hydrolysis of the polyvinyl acetate (PVAc) polymer. The degree of polymerisation determines the molecular weight and viscosity in solution. The degree of hydrolysis (saponification) signifies the extent of conversion of the Polyvinyl Acetate to the Polyvinyl Alcohol For example n (Degree of Hydrolysis) may be in the range of about 68.2 to about 99.8 mol. % and the MW (Weight Average Molecular Weight) may range from about 10.000 to about 190,000.

Hyaluronic acid (HA) is a polymer composed of repeating dimeric units of glucuronic acid and N-acetyl glucosamine. It may be of extremely high molecular weight (up to several million daltons) and forms the core of complex proteoglycan aggregates found in extracellular matrix. HA is comprised of linear, unbranching, polyanionic disaccharide units consisting of glucuronic acid (GlcUA) an N-acetyl glucosamine (GlcNAc) joined alternately by β-1-3 and β-1-4 glycosidic bonds (see below). It is a member of the glycosaminoglycan family which includes chondroitin sulphate, dermatin sulphate and heparan sulphate. Unlike other members of this family, it is not found covalently bound to proteins.

D-Glucuronic acid    N-acetyl glucosamine

When incorporated into a neutral aqueous solution hydrogen bond formation occurs between water molecules and adjacent carboxyl and N-acetyl groups. This imparts a conformational stiffness to the polymer, which limits its flexibility. The hydrogen bond formation results in the unique water-binding and retention capacity of the polymer. It also follows that the water-binding capacity is directly related to the molecular weight of the molecule. Up to six liters of water may be bound per gram of HA.

HA solutions are characteristically viscoelastic and pseudoplastic. This rheology is found even in very dilute solutions of the polymer where very viscous gels are formed. The viscoelastic property of HA solutions which is important in its use as a biomaterial is controlled by the concentration and molecular weight of the HA chains. The molecular weight of HA from different sources is polydisperse and highly variable ranging from $10^4$ to $10^7$ Da. The extrusion of HA through the cell membrane as it is produced permits unconstrained polymer elongation and hence a very high molecular weight molecule.

The phrase "polydispersity index" refers to the ratio of the "weight average molecular weight" to the "number average molecular weight" for a particular polymer; it reflects the distribution of individual molecular weights in a polymer sample.

The phrase "weight average molecular weight" refers to a particular measure of the molecular weight of a polymer. The weight average molecular weight is calculated as follows: determine the molecular weight of a number of polymer molecules; add the squares of these weights; and then divide by the total weight of the molecules.

The phrase "number average molecular weight" refers to a particular measure of the molecular weight of a polymer. The number average molecular weight is the common average of the molecular weights of the individual polymer molecules. It is determined by measuring the molecular weight of n polymer molecules, summing the weights, and dividing by n.

The terms "calculi" and "calculus" denote one or more masses or nodules of solid matter formed by growing together, by congelation, condensation, coagulation, induration, etc. Common synonyms, for example, are concretions, stones, clots, tones or lumps. Often, in an organism a concretion is a hard lump of mineral salts found in a hollow organ or duct. In one embodiment, concretion refers to stone-like objects found within an organ (e.g., the kidneys) of an organism.

The term "lumen" denotes the space enclosed by a tube-like structure or hollow organ, such as inside an artery, a vein, a kidney, a gall bladder, a ureter, a urinary bladder, a pancreas, a salivary gland, a small intestine or a large intestine (i.e., an opening, space, or cavity in a biological system). A lumen has an "inlet" and an "outlet" based on the direction of the flow of materials through the lumen. As used here "upstream" from a given object in a lumen means between said object and the inlet of the lumen; "downstream" from a given object in a lumen means between said object and the outlet of the lumen. "Peristalsis" as used herein refers to a series of coordinated, rhythmic muscle contractions. For example, it is an automatic and vital process that moves food through the digestive tract, urine from the kidneys through the ureters into the bladder, and bile from the gallbladder into the duodenum. Peristalsis moves material in a lumen towards the outlet of the lumen.

"Lithotripsy" as used herein refers to any procedure, surgery or technique that fragments or breaks up a stone.

"Lithiasis" as used herein refers to a common human ailment characterized by calculi or "stones" formed within a passage or lumen of a human.

Calculi

Calculi can develop in parts of the body, such as in the kidneys, pancreas, ureter and gallbladder. It is not uncommon for biological calculi to be referred to as stones, especially when they are composed of mineral salts. For example, calculi formed in the biliary system are called gallstones. Those that form in the bladder are often known as vesical calculi or bladder stones. Calculi occurring in the kidney are often called kidney stones. Calculi can also occur in the ureter; there they are usually the result of the incomplete passage of a calculi originating in a kidney. It is also possible to observe a calculi in a salivary duct or gland.

There are four main types of calculi observed biologically. The majority of calculi, about 75%, are calcium-containing, composed of calcium oxalate, sometimes mixed with calcium phosphate. Another 15% are composed of magnesium ammonium phosphate; these calculi are often referred to as "triple stones" or struvite stones. The bulk of the remaining stones are made up of uric acid or cystine (Cys-Cys). As mentioned above, when calculi are too large to pass spontaneously, medical intervention is often needed.

Polymers of the Invention

In certain embodiments a polymer plug is generated in situ by one or more physical phenomena, such as temperature, pH changes and/or ionic interactions. In other embodiment, the polymers used in a method of the invention are crosslinkable polymers. In certain embodiments the polymer plug generate in situ is non-tissue adhesive.

In one embodiment two solutions, a polymer solution and a crosslinker solution, are injected separately (e.g., through a dual lumen catheter) into a biological lumen wherein they gel, forming a polymer plug. Said polymer solution may comprise an anionic polymer, a cationic polymer or a non-ionically crosslinkable polymer. Such polymers may comprise one or more of the following: alginic acid, sodium alginate, potassium alginate, sodium gellan, potassium gellan, carboxy methyl cellulose, hyaluronic acid, and polyvinyl alcohol. The cross-linking of the polymer to form a polymer plug may be achieved with anionic crosslinking ions, cationic crosslinking ions, or non-ionic crosslinking agents. Crosslinking agents include, but are not limited to, one or more of the following: phosphate, citrate, borate, succinate, maleate, adipate, oxalate, calcium, magnesium, barium and strontium. Exemplary pairings of polymers and crosslinkers include anionic polymer monomers with cations, such as, for example, alginates with calcium, barium or magnesium; gellans with calcium, magnesium or barium; or hyaluronic acid with calcium. An example of an exemplary pairing of a non-ionic polymer with a chemical crosslinking agent is a polyvinyl alcohol with borate (at a slightly alkaline pH).

In addition, in certain embodiments, the polymer plugs of the invention may be formed from an aqueous solution of one or more inverse thermosensitive polymers. These polymer solutions are liquids below body temperature and gel at about body temperature. The polymer solution is prepared external of the body, i.e., at a temperature below body temperature. The polymer solution may be further chilled to prolong the time the gel stays in the liquid form upon introduction into the body. A preferred temperature is about 10° C. below the gelation temperature of the polymer solution.

In general, the inverse thermosensitive polymers used in the methods of the invention, which become a gel at or about body temperature, can be injected into a patient's body in a liquid form. The injected material upon reaching body temperature undergoes a transition from a liquid to a gel. The inverse thermosensitive polymers used in connection with the methods of the invention may comprise a block copolymer with inverse thermal gelation properties. The block copolymer can further comprise a polyoxyethylene-polyoxypropylene block copolymer, such as a biodegradable, biocompatible copolymer of polyethylene oxide and polypropylene oxide. Also, the inverse thermosensitive polymer can include a therapeutic agent.

The molecular weight of the inverse thermosensitive polymer is preferably between 1,000 and 50,000, more preferably between 5,000 and 35,000. Preferably the polymer is in an aqueous solution. For example, typical aqueous solutions contain about 5% to about 30% polymer, preferably about 10% to about 25%. The molecular weight of a suitable inverse thermosensitive polymer (such as a poloxamer or poloxamine) may be, for example, between 5,000 and 25,000, and more particularly between 7,000 and 20,000.

The pH of the inverse thermosensitive polymer formulation administered to the mammal is, generally, about 6.0 to about 7.8, which are suitable pH levels for injection into the mammalian body. The pH level may be adjusted by any suitable acid or base, such as hydrochloric acid or sodium hydroxide.

Suitable inverse thermosensitive polymers include polyoxyethylene-polyoxypropylene (PEO-PPO) block copolymers. Two examples are Pluronic® F127 and F108, which are PEO-PPO block copolymers with molecular weights of 12,600 and 14,600, respectively. Each of these compounds is available from BASF of Mount Olive, N.J. Pluronic® F108 at 12-25% concentration in phosphate buffered saline (PBS) is an example of a suitable inverse thermosensitive polymeric material. Pluronic® acid F127 at 12-25% concentration in PBS is another example of a suitable material. Low concentrations of dye (such as crystal violet), hormones, therapeutic agents, fillers, and antibiotics can be added to the inverse thermosensitive polymer. In general, other biocompatible, biodegradable PEO-PPO block copolymers that exist as a gel at body temperature and a liquid at below body temperature may also be used according to the present invention.

Notably, Pluronic® polymers have unique surfactant abilities and extremely low toxicity and immunogenic responses. These products have low acute oral and dermal toxicity and low potential for causing irritation or sensitization, and their general chronic and sub-chronic toxicity is low. In fact, Pluronic® polymers are among a small number of surfactants that have been approved by the FDA for direct use in medical applications and as food additives (BASF (1990) Pluronic® & Tetronic® Surfactants, BASF Co., Mount Olive, N.J.). Recently, several Pluronic® polymers have been found to enhance the therapeutic effect of drugs, and the gene transfer efficiency mediated by adenovirus (March K L, Madison J E, Trapnell B C. "Pharmacokinetics of adenoviral vector-mediated gene delivery to vascular smooth muscle cells: modulation by poloxamer 407 and implication for cardiovascular gene therapy" *Hum. Gene Therapy* 1995, 6, 41-53).

The average molecular weights of the poloxamers range from about 1,000 to greater than 16,000 daltons. Because the poloxamers are products of a sequential series of reactions, the molecular weights of the individual poloxamer molecules form a statistical distribution about the average molecular weight. In addition, commercially available poloxamers contain substantial amounts of poly(oxyethylene) homopolymer and poly(oxyethylene)/poly(oxypropylene) diblock polymers. The relative amounts of these byproducts increase as the molecular weights of the component blocks of the poloxamer increase. Depending upon the manufacturer, these byproducts may constitute from about 15 to about 50% of the total mass of the polymer.

The inverse thermosensitive polymers may be purified using a process for the fractionation of water-soluble polymers, comprising the steps of dissolving a known amount of the polymer in water, adding a soluble extraction salt to the polymer solution, maintaining the solution at a constant optimal temperature for a period of time adequate for two distinct phases to appear, and separating physically the phases. Additionally, the phase containing the polymer fraction of the preferred molecular weight may be diluted to the original volume with water, extraction salt may be added to achieve the original concentration, and the separation process repeated as needed until a polymer having a narrower molecular weight distribution than the starting material and optimal physical characteristics can be recovered.

In certain embodiments, a purified poloxamer or poloxamine has a polydispersity index from about 1.5 to about 1.0. In certain embodiments, a purified poloxamer or poloxamine has a polydispersity index from about 1.2 to about 1.0. In certain embodiments, a purified poloxamer or poloxamine has a polydispersity index from about 1.1 to about 1.0.

The aforementioned process consists of forming an aqueous two-phase system composed of the polymer and an appropriate salt in water. In such a system, a soluble salt can be added to a single phase polymer-water system to induce phase separation to yield a high salt, low polymer bottom phase, and a low salt, high polymer upper phase. Lower molecular weight polymers partition preferentially into the high salt, low polymer phase. Polymers that can be fractionated using this process include polyethers, glycols such as poly(ethylene glycol) and poly(ethylene oxide)s, polyoxyalkylene block copolymers such as poloxamers, poloxamines, and polyoxypropylene/polyoxybutylene copolymers, and other polyols, such as polyvinyl alcohol. The average molecular weight of these polymers may range from about 800 to greater than 100,000 daltons. See U.S. Pat. No. 6,761,824 (hereby incorporated by reference). The aforementioned purification process inherently exploits the differences in size and polarity, and therefore solubility, among the poloxamer molecules, the poly(oxyethylene) homopolymer and the poly(oxyethylene)/poly(oxypropylene) diblock byproducts. The polar fraction of the poloxamer, which generally includes the lower molecular weight fraction and the byproducts, is removed allowing the higher molecular weight fraction of poloxamer to be recovered. The larger molecular weight poloxamer recovered by this method has physical characteristics substantially different from the starting material or commercially available poloxamer including a higher average molecular weight, lower polydispersity and a higher viscosity in aqueous solution.

Other purification methods may be used to achieve the desired outcome. For example, WO 92/16484 discloses the use of gel permeation chromatography to isolate a fraction of poloxamer 188 that exhibits beneficial biological effects, without causing potentially deleterious side effects. The copolymer thus obtained had a polydispersity index of 1.07 or less, and was substantially saturated. The potentially harmful side effects were shown to be associated with the low molecular weight, unsaturated portion of the polymer, while the medically beneficial effects resided in the uniform higher molecular weight material. Other similarly improved copolymers were obtained by purifying either the polyoxypropylene center block during synthesis of the copolymer, or the copolymer product itself (e.g., U.S. Pat. Nos. 5,523,492 and 5,696, 298; both hereby incorporated by reference).

Further, a supercritical fluid extraction technique has been used to fractionate a polyoxyalkylene block copolymer as disclosed in U.S. Pat. No. 5,567,859 (hereby incorporated by reference). A purified fraction was obtained, which was composed of a fairly uniform polyoxyalkylene block copolymer having a polydispersity of less than 1.17. According to this method, the lower molecular weight fraction was removed in a stream of carbon dioxide maintained at a pressure of 2200 pounds per square inch (psi) and a temperature of 40° C.

Additionally, U.S. Pat. No. 5,800,711 (hereby incorporated by reference) discloses a process for the fractionation of polyoxyalkylene block copolymers by the batchwise removal of low molecular weight species using a salt extraction and liquid phase separation technique. Poloxamer 407 and poloxamer 188 were fractionated by this method. In each case, a copolymer fraction was obtained which had a higher average molecular weight and a lower polydispersity index as compared to the starting material. However, the changes in polydispersity index were modest and analysis by gel permeation chromatography indicated that some low-molecular-weight material remained. The viscosity of aqueous solutions of the fractionated polymers was significantly greater than the viscosity of the commercially available polymers at temperatures between 10° C. and 37° C., an important property for some medical and drug delivery applications. Nevertheless, some of the low molecular weight contaminants of these polymers are thought to cause deleterious side effects when used inside the body, making it especially important that they be removed in the fractionation process. As a consequence, polyoxyalkylene block copolymers fractionated by this process are not appropriate for all medical uses.

In a preferred embodiment, the polymers used are block polymers such as polyoxyethylene-polyoxypropylene (PEO-PPO) block polymers of the general structure A-B, (A-B)$_n$, A-B-A (e.g., Pluronic®), or (A-B-A)$_n$ with A being the PEO part and B being the PPO part and n being greater than 1. In another preferred embodiment, the polymers used are branched polymers of polyoxyethylene-polyoxypropylene (PEO-PPO) like tetra-functional poloxamines (e.g., Tetronic®).

Methods of the Invention

The present invention provides an approach to the treatment of lithiasis. In one embodiment a polymer is injected between the inlet of a lumen and a calculi in said lumen to form a polymer plug which occludes the lumen; the subsequent action of peristalsis causes the polymer plug to traverse the lumen, forcing the calculi out of the lumen.

One aspect of the present invention relates to a method of treating lithiasis, comprising the steps of:
injecting into a lumen of a mammal at a first position upstream from a calculi a first composition, wherein said first composition does not contact said calculi; optionally injecting into said lumen at a second position upstream from said calculi a second composition, wherein said second composition does not contact said calculi; thereby forming a polymer plug; and
allowing peristalsis to cause said polymer plug to traverse said lumen, thereby forcing said calculi from said lumen.

In certain embodiments, the present invention relates to the aforementioned method, wherein said second composition is injected into said lumen.

In certain embodiments, the present invention relates to the aforementioned method, wherein said first position is between about 1 cm and about 5 cm upstream of said calculi.

In certain embodiments, the present invention relates to the aforementioned method, wherein said first position is between about 2 cm and about 4 cm upstream of said calculi.

In certain embodiments, the present invention relates to the aforementioned method, wherein said first position is about 3 cm upstream of said calculi.

In certain embodiments, the present invention relates to the aforementioned method, wherein the distance between said first position and said second position is less than about 3 mm.

In certain embodiments, the present invention relates to the aforementioned method, wherein the distance between said first position and said second position is less than about 1 mm.

In certain embodiments, the present invention relates to the aforementioned method, wherein the distance between said first position and said second position is less than about 0.5 mm.

In certain embodiments, the present invention relates to the aforementioned method, wherein the distance between said first position and said second position is less than about 0.1 mm.

In certain embodiments, the present invention relates to the aforementioned method, wherein said first composition is injected into said lumen through a percutaneous access device.

In certain embodiments, the present invention relates to the aforementioned method, wherein said first composition is injected into said lumen through a catheter or a syringe.

In certain embodiments, the present invention relates to the aforementioned method, wherein the catheter is a dual lumen catheter or a triple lumen catheter.

In certain embodiments, the present invention relates to the aforementioned method, wherein said lumen is or is a portion of a kidney, gall bladder, ureter, urinary bladder, pancreas, salivary gland, small intestine or large intestine.

In certain embodiments, the present invention relates to the aforementioned method, wherein said lumen is or is a portion of a ureter or kidney.

In certain embodiments, the present invention relates to the aforementioned method, wherein said calculi is a kidney stone, pancreatic stone, salivary stone, or biliary stone.

In certain embodiments, the present invention relates to the aforementioned method, wherein said calculi is a kidney stone.

In certain embodiments, the present invention relates to the aforementioned method, wherein said mammal is a human.

In certain embodiments, the present invention relates to the aforementioned method, wherein said second composition comprises a contrast-enhancing agent.

In certain embodiments, the present invention relates to the aforementioned method, wherein said contrast-enhancing agent is selected from the group consisting of radiopaque materials, paramagnetic materials, heavy atoms, transition metals, lanthanides, actinides, dyes, and radionuclide-containing materials.

Another aspect of the present invention relates to a method of treating lithiasis, comprising the steps of:

injecting into a lumen of a mammal at a first distance upstream from a calculi a first composition comprising an inverse thermosensitive polymer, wherein said first composition does not contact said calculi; thereby forming a polymer plug;

optionally injecting into said lumen at a second distance upstream from said calculi a second composition, wherein said second composition does not contact said calculi; and allowing peristalsis to cause said polymer plug to traverse said lumen, thereby forcing said calculi from said lumen.

In certain embodiments, the present invention relates to the aforementioned method, wherein said second composition is injected into said lumen.

In certain embodiments, the present invention relates to the aforementioned method, wherein said second composition is injected into said lumen.

In certain embodiments, the present invention relates to the aforementioned method, wherein said first position is between about 1 cm and about 5 cm upstream of said calculi.

In certain embodiments, the present invention relates to the aforementioned method, wherein said first position is between about 2 cm and about 4 cm upstream of said calculi.

In certain embodiments, the present invention relates to the aforementioned method, wherein said first position is about 3 cm upstream of said calculi.

In certain embodiments, the present invention relates to the aforementioned method, wherein the distance between said first position and said second position is less than about 3 mm.

In certain embodiments, the present invention relates to the aforementioned method, wherein the distance between said first position and said second position is less than about 1 mm.

In certain embodiments, the present invention relates to the aforementioned method, wherein the distance between said first position and said second position is less than about 0.5 mm.

In certain embodiments, the present invention relates to the aforementioned method, wherein the distance between said first position and said second position is less than about 0.1 mm.

In certain embodiments, the present invention relates to the aforementioned method, wherein said first composition is injected into said lumen through a percutaneous access device.

In certain embodiments, the present invention relates to the aforementioned method, wherein said first composition is injected into said lumen through a catheter or a syringe.

In certain embodiments, the present invention relates to the aforementioned method, wherein the catheter is a dual lumen catheter or a triple lumen catheter.

In certain embodiments, the present invention relates to the aforementioned method, wherein said lumen is or is a portion of a kidney, gall bladder, ureter, urinary bladder, pancreas, salivary gland, small intestine or large intestine.

In certain embodiments, the present invention relates to the aforementioned method, wherein said lumen is or is a portion of a ureter or kidney.

In certain embodiments, the present invention relates to the aforementioned method, wherein said calculi is a kidney stone, pancreatic stone, salivary stone, or biliary stone.

In certain embodiments, the present invention relates to the aforementioned method, wherein said calculi is a kidney stone.

In certain embodiments, the present invention relates to the aforementioned method, wherein said mammal is a human.

In certain embodiments, the present invention relates to the aforementioned method, wherein said second composition comprises a contrast-enhancing agent.

In certain embodiments, the present invention relates to the aforementioned method, wherein said contrast-enhancing agent is selected from the group consisting of radiopaque materials, paramagnetic materials, heavy atoms, transition metals, lanthanides, actinides, dyes, and radionuclide-containing materials.

In certain embodiments, the present invention relates to the aforementioned method, wherein said inverse thermosensitive polymer is a block copolymer, random copolymer, graft polymer, or branched copolymer.

In certain embodiments, the present invention relates to the aforementioned method, wherein said inverse thermosensitive polymer is a block polymer or a branched copolymer.

In certain embodiments, the present invention relates to the aforementioned method, wherein said inverse thermosensitive polymer is an optionally purified poloxamer or poloxamine.

In certain embodiments, the present invention relates to the aforementioned method, wherein said inverse thermosensitive polymer is optionally purified and selected from the group consisting of poloxamine 1107, poloxamine 1307, poloxamer 338 and poloxamer 407.

In certain embodiments, the present invention relates to the aforementioned method, wherein said inverse thermosensitive polymer is an optionally purified poloxamer 407.

In certain embodiments, the present invention relates to the aforementioned method, wherein said first composition has a transition temperature of between about 10° C. and 40° C.

In certain embodiments, the present invention relates to the aforementioned method, wherein said first composition has a transition temperature of between about 15° C. and 30° C.

In certain embodiments, the present invention relates to the aforementioned method, wherein said first composition has a transition temperature of about 25° C.

In certain embodiments, the present invention relates to the aforementioned method, wherein said first composition comprises about 5% to about 30% of said inverse thermosensitive polymer.

In certain embodiments, the present invention relates to the aforementioned method, wherein said first composition comprises about 10% to about 25% said inverse thermosensitive polymer.

In certain embodiments, the present invention relates to the aforementioned method, wherein the inverse thermosensitive polymer has a polydispersity index from about 1.5 to 1.0.

In certain embodiments, the present invention relates to the aforementioned method, wherein the inverse thermosensitive polymer has a polydispersity index from about 1.2 to 1.0.

In certain embodiments, the present invention relates to the aforementioned method, wherein the inverse thermosensitive polymer has a polydispersity index from about 1.1 to 1.0.

In certain embodiments, the present invention relates to the aforementioned method, wherein said inverse thermosensitive polymer is an optionally purified poloxamer or poloxamine; and said first composition has a transition temperature of between about 10° C. and 40° C.

In certain embodiments, the present invention relates to the aforementioned method, wherein said inverse thermosensitive polymer is an optionally purified poloxamer or poloxamine; and said first composition has a transition temperature of between about 15° C. and 30° C.

In certain embodiments, the present invention relates to the aforementioned method, wherein said inverse thermosensitive polymer is an optionally purified poloxamer or poloxamine; and said first composition has a transition temperature of about 25° C.

Another aspect of the present invention relates to a method of treating lithiasis, comprising the steps of:

injecting into a lumen of a mammal at a first distance upstream from a calculi a first composition, wherein said first composition does not contact said calculi;

injecting into said lumen at a second distance upstream from said calculi a second composition, wherein said second composition does not contact said calculi; wherein said first composition and said second composition admix, thereby forming a polymer plug;

optionally injecting into said lumen at a third distance upstream from said calculi a third composition, wherein said third composition does not contact said calculi; and allowing peristalsis to cause said polymer plug to traverse said lumen, thereby forcing said calculi from said lumen.

In certain embodiments, the present invention relates to the aforementioned method, wherein said third composition is injected into said lumen.

In certain embodiments, the present invention relates to the aforementioned method, wherein said second composition is injected into said lumen.

In certain embodiments, the present invention relates to the aforementioned method, wherein said first position is between about 1 cm and about 5 cm upstream of said calculi.

In certain embodiments, the present invention relates to the aforementioned method, wherein said first position is between about 2 cm and about 4 cm upstream of said calculi.

In certain embodiments, the present invention relates to the aforementioned method, wherein said first position is about 3 cm upstream of said calculi.

In certain embodiments, the present invention relates to the aforementioned method, wherein the distance between said first position and said second position is less than about 3 mm.

In certain embodiments, the present invention relates to the aforementioned method, wherein the distance between said first position and said second position is less than about 1 mm.

In certain embodiments, the present invention relates to the aforementioned method, wherein the distance between said first position and said second position is less than about 0.5 mm.

In certain embodiments, the present invention relates to the aforementioned method, wherein the distance between said first position and said second position is less than about 0.1 mm.

In certain embodiments, the present invention relates to the aforementioned method, wherein said first and second compositions are injected into said lumen through a percutaneous access device.

In certain embodiments, the present invention relates to the aforementioned method, wherein said first and second compositions are injected into said lumen through a catheter or a syringe.

In certain embodiments, the present invention relates to the aforementioned method, wherein the catheter is a dual lumen catheter or a triple lumen catheter.

In certain embodiments, the present invention relates to the aforementioned method, wherein said lumen is or is a portion of a kidney, gall bladder, ureter, urinary bladder, pancreas, salivary gland, small intestine or large intestine.

In certain embodiments, the present invention relates to the aforementioned method, wherein said lumen is or is a portion of a ureter or kidney.

In certain embodiments, the present invention relates to the aforementioned method, wherein said calculi is a kidney stone, pancreatic stone, salivary stone, or biliary stone.

In certain embodiments, the present invention relates to the aforementioned method, wherein said calculi is a kidney stone.

In certain embodiments, the present invention relates to the aforementioned method, wherein said mammal is a human.

In certain embodiments, the present invention relates to the aforementioned method, wherein said second composition comprises a contrast-enhancing agent.

In certain embodiments, the present invention relates to the aforementioned method, wherein said contrast-enhancing agent is selected from the group consisting of radiopaque materials, paramagnetic materials, heavy atoms, transition metals, lanthanides, actinides, dyes, and radionuclide-containing materials.

In certain embodiments, the present invention relates to the aforementioned method, wherein said first composition comprises an anionic, cationic, or non-ionically crosslinkable polymer.

In certain embodiments, the present invention relates to the aforementioned method, wherein said first composition comprises a polymer selected from the group consisting of alginic acid, sodium alginate, potassium alginate, sodium gellan, potassium gellan, carboxy methyl cellulose, hyaluronic acid and polyvinyl alcohol.

In certain embodiments, the present invention relates to the aforementioned method, wherein said second composition comprises phosphate, citrate, borate, succinate, maleate, adipate, oxalate, calcium, magnesium, barium, strontium, or a combination thereof.

In certain embodiments, the present invention relates to the aforementioned method, wherein said first composition comprises a polymer selected from the group consisting of alginic acid, sodium alginate, potassium alginate, sodium gellan and potassium gellan; and said second composition comprises calcium, magnesium or barium.

In certain embodiments, the present invention relates to the aforementioned method, wherein said first composition comprises a polymer selected from the group consisting of alginic acid, sodium alginate or potassium alginate; and said second composition comprises calcium.

In certain embodiments, the present invention relates to the aforementioned method, wherein said first composition comprises a polymer selected from the group consisting of sodium gellan and potassium gellan; and said second composition comprises magnesium.

In certain embodiments, the present invention relates to the aforementioned method, wherein said first composition comprises hyaluronic acid; and said second composition comprises calcium.

In certain embodiments, the present invention relates to the aforementioned method, wherein said first composition comprises polyvinyl alcohol; and said second composition comprises borate.

In one embodiment the polymer solution can be introduced through a catheter. The catheter may be a dilatation catheter. In one embodiment, the catheter is 3-10 French in size, and more preferably 3-6 French. In another embodiment, a catheter can be used to dispense one or more fluids other than, or in addition to, the polymer solution. In said embodiment the catheter may be a multiple lumen catheter with one lumen for the delivery of the polymer solution, other lumen for the delivery of other fluids such as a contrast agent solution.

In another embodiment, the syringe or other mechanism may be used to inject the polymer solution into the body can be, for example, a 1-100 cc syringe, a 1-50 cc syringe or a 1-5 cc. Pressure applied to the syringe can be applied by hand or by an automated syringe pusher.

EXEMPLIFICATION

The invention now being generally described, it will be more readily understood by reference to the following examples, which are included merely for purposes of illustration of certain aspects and embodiments of the present invention, and are not intended to limit the invention.

Example 1

Gelation Temperature of Selected Pluronic® and Tetronic® Polymer Solutions

The polymer was weighed into a plastic tube. To achieve the required concentration the weight was multiplied by 4, for 25 weight percent (w %), and by 5, for 20 weight percent (w %), and the required final weight was achieved by adding saline. The solutions were placed in the fridge at 4° C. and usually were ready within 24 hours. Gelation points were measured in a Brookfield viscometer and the point at which viscosity exceeded the range of the plate/cone (greater than about 102,000 cP) was called the gelation temperature.

TABLE 1

Gelation Temperature of Selected Inverse Thermosensitive Polymer Solutions in Saline.

| polymer | concentration | temperature |
| --- | --- | --- |
| Tetronic 1107 | 25 w % | 27° C. |
| Tetronic 1107 | 20 w % | 34° C. |
| Purified Tetronic 1107 | 25 w % | 22° C. |
| Purified Tetronic 1107 | 20 w % | 32.5° C. |
| Tetronic 1307 | 25 w % | 24.5° C. |
| Tetronic 1307 | 20 w % | 31° C. |
| Purified Tetronic 1307 | 25 w % | 20° C. |
| Purified Tetronic 1307 | 20 w % | 26° C. |
| Pluronic F108 | 25 w % | 26° C. |
| Pluronic F108 | 20 w % | 60° C. |
| Purified Pluronic F108 | 25 w % | 19° C. |
| Purified Pluronic F108 | 20 w % | 26° C. |

Example 2

Gelation Temperature of Selected Pluronic® and Tetronic® Polymer Solutions with Iodinated Contrast Agent Purified polymers were weighed into 50 mL centrifuge tubes and a 1:1 mixture of saline and 100% Omnipaque 300 were added until a specific weight percentage was reached. Gelation points were measured in a Brookfield viscometer and the point at which the viscosity exceeded the range of the plate/cone (greater than about 102,000 cP) was called the gelation point. All solutions were further heated to 37° C. to ascertain that the material still exceeded the viscosity range and remained a gel. All gels passed.

TABLE 2

Gelation Temperature of Purified Inverse Thermosensitive Polymer Solutions containing 50 w % Omnipaque 300

| polymer | concentration | temperature |
| --- | --- | --- |
| Purified Tetronic 1107 | 20 w % | 24° C. |
| Purified Tetronic 1307 | 21 w % | 26.5° C. |
| Purified Pluronic F108 | 18 w % | 21.5° C. |
| Purified Pluronic F127 | 18 w % | 18° C. |

Example 3

Dissolution Time Under Static Conditions in Saline

The dissolution of the purified poloxamer 407 gel was tested by injecting 0.5 milliliter of the gel into a petri dish covered in saline at 37° C. The gel was visualized by small addition of methylene blue and the dissolution of the gel was followed visually. Two different shapes of the gels were used for the dissolution tests: a sphere which has the least amount of surface area; and a string, which has the highest surface area, in which a 20 gauge syringe was used to extrude the string of polymer onto the bottom of the Petri dish.

The petri dish was not disturbed and every minute, the petri dish was observed visually and complete dissolution was confirmed by swirling the petri dish.

Figure 1:
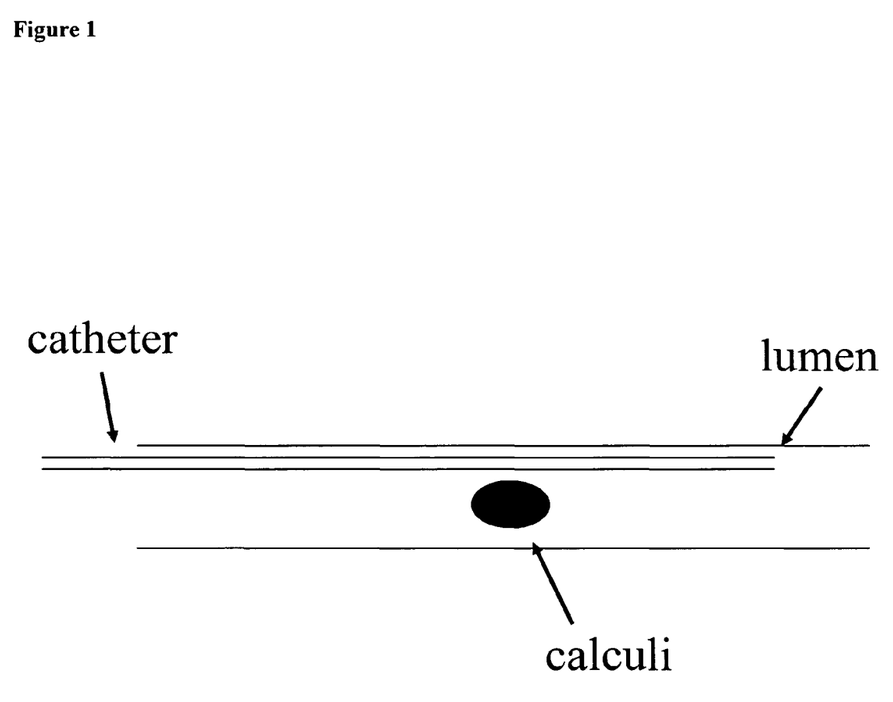
FIG. 1 depicts the deployment of a catheter into a lumen containing a calculi.
Figure 2:
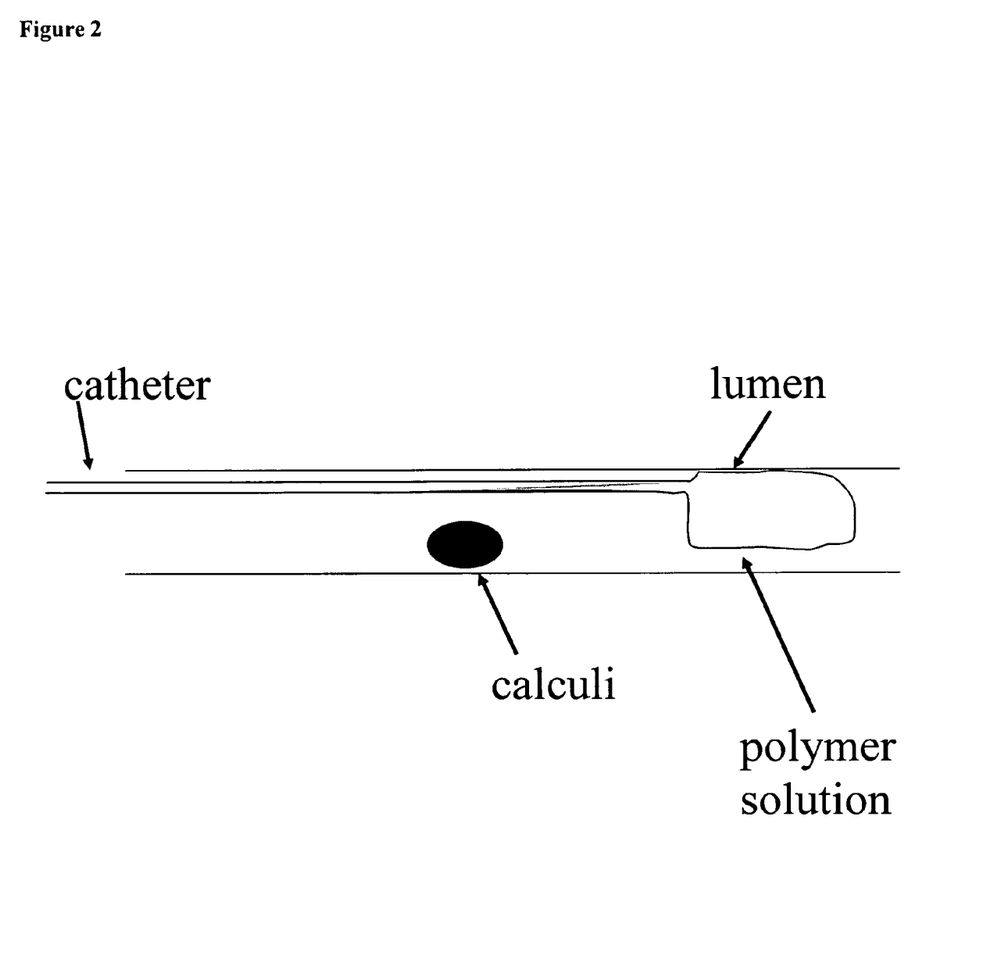
FIG. 2 depicts one embodiment of the deployment of a polymer in a lumen at a position upstream from a calculi.
Figure 3:
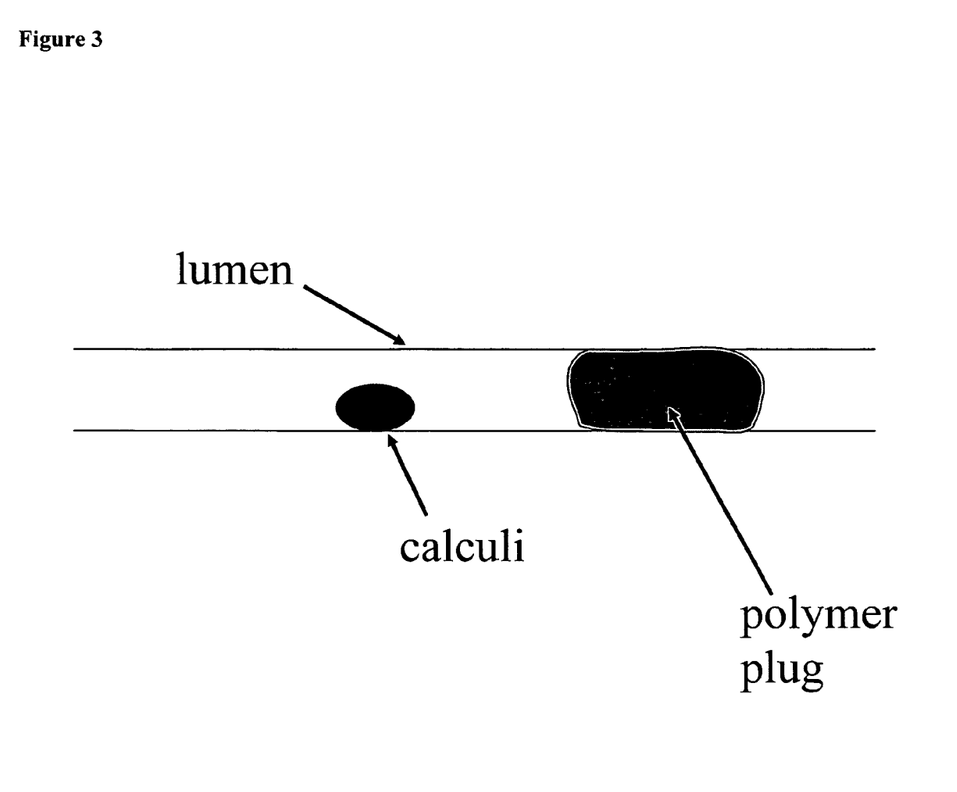
FIG. 3 depicts the position of the polymer plug and calculi before peristaltic motion.
Figure 4:
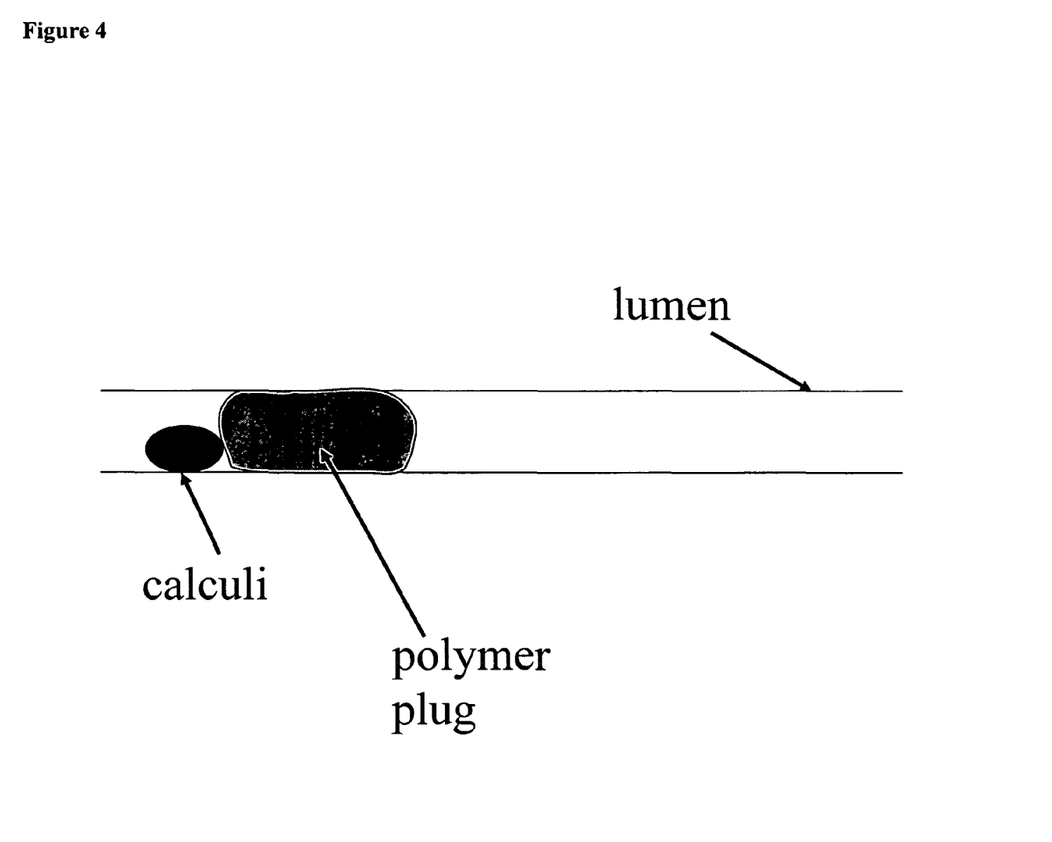
FIG. 4 depicts the effect of peristalsis (i.e. the movement of the polymer plug towards the outlet of the lumen and the resulting expulsion of the calculi).
Figure 5:
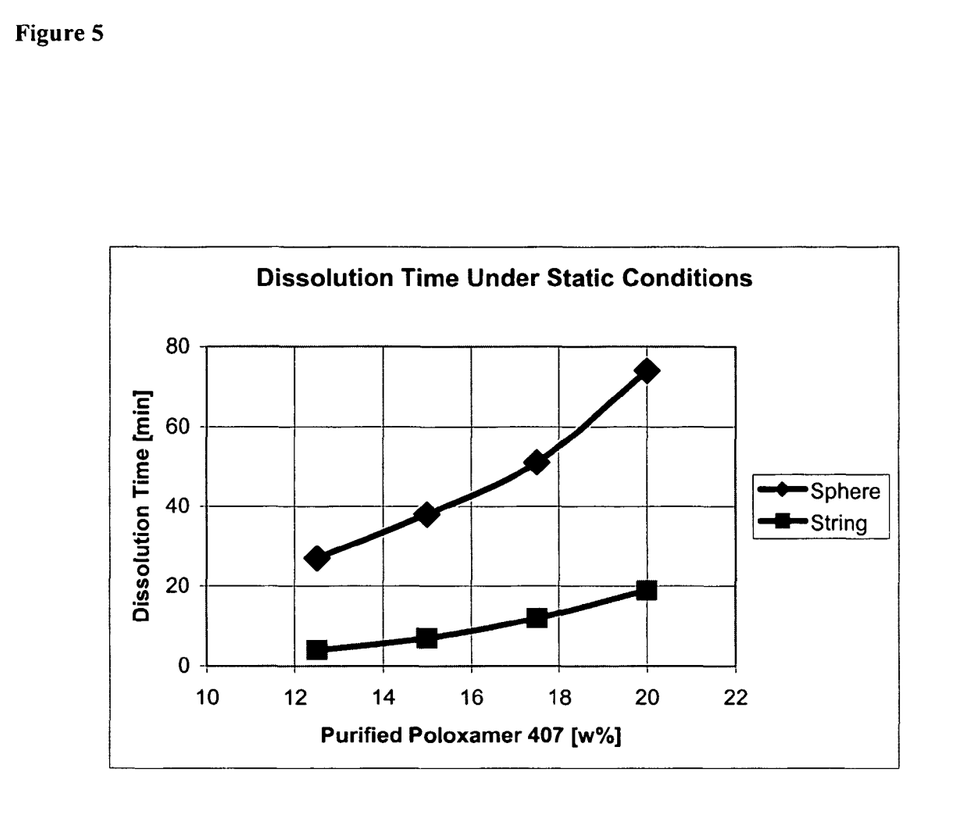
FIG. 5 depicts dissolution times under static conditions for purified poloxamer 407 as function of concentration (see Example 3).

The dissolution was dependent on the concentration of the polymer. The lower the polymer concentration, the faster the gel dissolved as depicted in the FIG. 5. Further, the dissolution was dependent on the surface area in direct contact with the surrounding liquid, the sphere-shaped gel taking longer to dissolve than the string.

These in-vitro experiments probably still overestimate the real dissolution times as there was no pulsatile force on the gel, which would probably speed up the dissolution.

Example 4

Dissolution Time Under Static Conditions in Urine

The dissolution of the 22.5% purified poloxamer 407 gel was tested by injecting 2.5 milliliter of the gel into a petri dish covered in about 100 mL urine at 37° C. A syringe without a needle was used to extrude a string of polymer onto the bottom of the Petri dish. The gel was visualized by small addition of methylene blue and the dissolution of the gel was followed visually. Upon extrusion the string broke in two. The petri dish was not disturbed and every minute, the petri dish was observed visually and complete dissolution was confirmed by swirling the petri dish. The complete dissolution time (about 26 minutes) was identical for the two strings.

Example 5

Pig Ureter In-Vivo Experiments

A 22.5 w% solution of purified Poloxamer PF127, colored with methylene blue, in a Medallion 5 ml syringe was used. In each of the three pigs, an artificial stone, made of plaster of Paris, was surgically implanted in the right ureter a few centimeters above the site of the incision. The solution was then injected behind the stone through the same incision site, using a 3F catheter [Embocath HIC 100 from BioSphere Medical, lot# 03W-6930]. Immediately prior to the injection the catheter was flushed with 10 cc of cold saline to keep it cool during the injection and avoid hardening of the polymer within the catheter. Each procedure was monitored with a camera inserted in the ureter between the stone and the incision site.

Pig #1—3 ml of solution were injected behind the stone that occluded ca. ¼ to ⅓ of the cross-section of the ureter, and created a well visible blue polymer plug that completed occluded the ureter behind the stone. After a little over 1 minute, the polymer plug or some urine accumulating behind it created contraction waves of the ureteral walls (peristalsis) which forced the plug to slide forward towards the camera and out of the ureter, carrying with it the entire stone, without any need for lithotripsy.

Pig #2—Same as the $1^{st}$ pig but the stone was slightly larger, and immediately after the injection of the polymer lithotripsy (EHL) was used to break the stone into small fragments. Within one minute of the completion of lithotripsy peristalsis started and the stone debris were pushed by the sliding plug out of the ureter.

Pig #3—Same as the 2nd pig but the stone was even larger. Within one minute of the completion of lithotripsy peristalsis started and the stone debris were pushed by the sliding plug out of the ureter.

Incorporation by Reference

All of the U.S. patents and U.S patent application publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of treating lithiasis, comprising the steps of:
   injecting into a lumen of a mammal at a first distance upstream from a calculi a first composition comprising an inverse thermosensitive polymer, wherein said first composition does not initially contact said calculi; thereby forming a polymer plug; and
   removing the calculi from the lumen by movement of the polymer plug by peristalsis to traverse said lumen, thereby forcing said calculi from said lumen.

2. The method of claim 1, further comprising injecting into said lumen a second composition at a second distance upstream from said calculi wherein said second composition does not contact said calculi.

3. The method of claim 1, wherein said first distance is between about 1 cm and about 5 cm upstream of said calculi.

4. The method of claim 1, wherein said first distance is between about 2 cm and about 4 cm upstream of said calculi.

5. The method of claim 1, wherein said first distance is about 3 cm upstream of said calculi.

6. The method of claim 2, wherein the distance between said first distance and said second distance is less than about 3 mm.

7. The method of claim 2, wherein the distance between said first distance and said second distance is less than about 1 mm.

8. The method of claim 2, wherein the distance between said first distance and said second distance is less than about 0.5 mm.

9. The method of claim 2, wherein the distance between said first distance and said second distance is less than about 0.1 mm.

10. The method of claim 1, wherein said first composition is injected into said lumen through a percutaneous access device.

11. The method of claim 1, wherein said first composition is injected into said lumen through a catheter or a syringe.

12. The method of claim 11, wherein the catheter is a dual lumen catheter or a triple lumen catheter.

13. The method of claim 1, wherein said lumen is or is a portion of a kidney, gall bladder, ureter, urinary bladder, pancreas, salivary gland, small intestine, or large intestine.

14. The method of claim 1, wherein said lumen is or is a portion of a ureter or kidney.

15. The method of claim 1, wherein said calculi is a kidney stone, pancreatic stone, salivary stone, or biliary stone.

16. The method of claim 1, wherein said calculi is a kidney stone.

17. The method of claim 1, wherein said mammal is a human.

18. The method of claim 2, wherein said second composition comprises a contrast-enhancing agent.

19. The method of claim 18, wherein said contrast-enhancing agent is selected from the group consisting of radiopaque materials, paramagnetic materials, heavy atoms, transition metals, lanthanides, actinides, dyes, and radionuclide-containing materials.

20. The method of claim 17, wherein said inverse thermosensitive polymer is a block copolymer, random copolymer, graft polymer, or branched copolymer.

21. The method of claim 17, wherein said inverse thermosensitive polymer is a block polymer or a branched copolymer.

22. The method of claim 17, wherein said inverse thermosensitive polymer is an optionally purified poloxamer or poloxamine.

23. The method of claim 17, wherein said inverse thermosensitive polymer is optionally purified and selected from the group consisting of poloxamine 1107, poloxamine 1307, poloxamer 338 and poloxamer 407.

24. The method of claim 17, wherein said inverse thermosensitive polymer is an optionally purified poloxamer 407.

25. The method of claim 17, wherein said first composition has a transition temperature of between about 10° C. and 40° C.

26. The method of claim 17, wherein said first composition has a transition temperature of between about 15° C. and 30° C.

27. The method of claim 17, wherein said first composition comprises about 5% to about 30% of said inverse thermosensitive polymer.

28. The method of claim 17, wherein said first composition comprises about 10% to about 25% said inverse thermosensitive polymer.

29. The method of claim 17, wherein the inverse thermosensitive polymer has a polydispersity index from about 1.5 to 1.0.

30. The method of claim 17, wherein said inverse thermosensitive polymer is an optionally purified poloxamer or poloxamine; and said first composition has a transition temperature of between about 10° C. and 40° C.

31. The method of claim 17, wherein said inverse thermosensitive polymer is an optionally purified poloxamer or poloxamine; and said first composition has a transition temperature of between about 15° C. and 30° C.

32. The method of claim 17, wherein said lumen is or is a portion of a kidney, gall bladder, ureter, urinary bladder, pancreas, salivary gland, small intestine or large intestine.

33. The method of claim 17, wherein said lumen is or is a portion of a ureter or kidney.

34. The method of claim 17, wherein said calculi is a kidney stone, pancreatic stone, salivary stone, or biliary stone.

35. The method of claim 17, wherein said calculi is a kidney stone.

36. The method of claim 1, wherein the polymer plug is non-tissue adhesive.

37. The method of claim 2, wherein the second composition comprises a cross-linker solution.

* * * * *